(12) United States Patent
Cammarata et al.

(10) Patent No.: US 7,621,181 B2
(45) Date of Patent: Nov. 24, 2009

(54) FLUID LEVEL DETECTOR AND ANALYZER

(75) Inventors: Charles Cammarata, Andover, NJ (US); Timothy Olsen, Glenwood, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 377 days.

(21) Appl. No.: 11/402,254

(22) Filed: Apr. 12, 2006

(65) Prior Publication Data

US 2007/0240505 A1 Oct. 18, 2007

(51) Int. Cl.
*G01F 23/00* (2006.01)
(52) U.S. Cl. .................. 73/304 R; 73/290 R; 73/290 V
(58) Field of Classification Search ............... 73/304 R, 73/290 R, 290 V
See application file for complete search history.

(56) References Cited

U.S. PATENT DOCUMENTS

| | | | | |
|---|---|---|---|---|
| 3,995,212 | A * | 11/1976 | Ross ........................... | 324/642 |
| 4,818,492 | A | 4/1989 | Shimizu | |
| 4,970,468 | A | 11/1990 | Ishizawa et al. | |
| 5,049,826 | A | 9/1991 | Sasao | |
| 5,083,470 | A | 1/1992 | Davis et al. | |
| 5,212,992 | A | 5/1993 | Calhoun et al. | |
| 5,270,210 | A | 12/1993 | Weyrauch et al. | |
| 5,365,783 | A | 11/1994 | Zweifel | |
| 5,400,651 | A * | 3/1995 | Welch ....................... | 73/290 R |
| 5,550,059 | A | 8/1996 | Boger et al. | |
| 5,602,333 | A * | 2/1997 | Larrabee et al. ............... | 73/149 |
| 5,648,727 | A | 7/1997 | Tyberg et al. | |
| 6,087,182 | A * | 7/2000 | Jeng et al. ..................... | 436/66 |
| 6,212,949 | B1 | 4/2001 | Inder et al. | |
| 6,255,954 | B1 * | 7/2001 | Brown et al. ................. | 340/603 |
| 6,270,726 | B1 | 8/2001 | Tyberg et al. | |
| 6,365,109 | B1 * | 4/2002 | Jeng et al. ..................... | 422/99 |
| 6,377,052 | B1 * | 4/2002 | McGinnis et al. ........... | 324/446 |
| 6,426,045 | B1 * | 7/2002 | Jeng et al. ................. | 422/82.05 |
| 6,433,560 | B1 * | 8/2002 | Hansen et al. ............... | 324/668 |
| 6,773,922 | B2 * | 8/2004 | Jeng et al. ..................... | 436/66 |
| 6,818,134 | B2 * | 11/2004 | Lemmon et al. ............. | 210/656 |
| 7,078,910 | B2 * | 7/2006 | Hirthe et al. ................. | 324/446 |
| 7,106,075 | B2 * | 9/2006 | Hu .............................. | 324/698 |
| 7,150,190 | B2 | 12/2006 | Krufka et al. | |
| 7,270,956 | B2 * | 9/2007 | Bazan et al. .................... | 435/6 |
| 7,282,372 | B2 | 10/2007 | VanBrunt et al. | |
| 7,318,344 | B2 * | 1/2008 | Heger ....................... | 73/304 C |
| 2003/0048432 | A1 * | 3/2003 | Jeng et al. ..................... | 356/39 |
| 2004/0099531 | A1 * | 5/2004 | Srinivasan et al. .......... | 204/412 |

(Continued)

*Primary Examiner*—Hezron Williams
*Assistant Examiner*—Rodney T Frank
(74) *Attorney, Agent, or Firm*—Chien Yuan, Esq

(57) ABSTRACT

An electronic technique is used for identifying a fluid and determining its level in a container. Specifically, impedance spectroscopy is applied to fluid handling probes such as those employed by automated chemical and immunoassay analyzers to provide superior sensitivity for fluid level detection as well as discernible "spectral signatures" (impedance spectra) that can be automatically analyzed to identify diverse materials. These include, but are not limited to, blood serum, blood plasma, gelsep, red blood cell layers, chemical reagents associated with immunoassay blood testing and foam atop fluid surfaces. In operation, incident electronic signal is compared with a reflected electronic signal to obtain signal characteristics that can be used to identify the type of liquid. In addition, characteristics of the reflected electronic signal (e.g., phase shift, etc.) as compared with the incident electronic signal are used to determine the level of fluid in a container.

17 Claims, 4 Drawing Sheets

U.S. PATENT DOCUMENTS

2004/0106163 A1 * 6/2004 Workman et al. ............. 435/14
2005/0010090 A1 * 1/2005 Acosta et al. ............... 600/316
2005/0274611 A1 * 12/2005 Schlichting ................. 204/401

* cited by examiner

FLUID LEVEL DETECTOR AND ANALYZER

BACKGROUND OF THE INVENTION

1. Field of the Invention

The present invention generally relates to an electronic technique for identifying a fluid and determining its level in a container, and more particularly, to the application of impedance spectroscopy to fluid handling probes such as those employed by automated chemical and immunoassay analyzers.

2. Background

Current fluid level detection technologies typically employ electronic techniques to measure changes in conductance or capacitance as an analyzer's fluid transfer pipette contacts a fluid surface. Each method effectively identifies fluid surfaces, but each also bears significant inherent disadvantages within the context of automated chemical and immunoassay analyzers.

Conductance techniques require two conducting points, both of which are typically inserted into the fluid of interest. These are typically incorporated into an assembly comprised of a conductive pipette probe positioned in close proximity to a wire-like conductor. Thus, a circuit is completed when the tip of the assembly is inserted into a fluid. Unfortunately, such configurations are mechanically delicate, difficult to clean and are prone to contaminate fluids into which they are inserted.

Capacitance techniques require two conducting surfaces. In contrast to the conductance technique, capacitance techniques require the insertion of only one conductor into the fluid of interest. This is typically the pipette probe itself, so the resulting physical configuration is often more robust than those employed for conductance measurements. However, as the second conductor, capacitance measurements require placement of an effective ground plane in contact with the fluid container in order to achieve sufficient sensitivity. As such, they work poorly, if at all, with fluid containers positioned at any distance from a ground plane. Unfortunately, this problematic situation frequently arises when automated analyzers need to handle small volume containers known as tube top cups. Further, capacitance-based methodologies are vulnerable to changes in ambient conditions including atmospheric variations and the proximity of nearby objects such as laboratory personnel.

In addition to these drawbacks, both capacitance and conductance techniques lack the ability to identify fluids, and are unable to distinguish fluid surfaces from air bubbles situated atop them. The inadequacy renders analyzers vulnerable to fluid sampling failure if the pipette aspirates air bubbles instead of fluid.

U.S. Pat. No. 5,275,951, Liquid level sensing Method and Device, describes an immunochemistry analyzer that employs a bi-static RF transmitter/receiver pair for determination of liquid levels in conjunction with electronic circuitry to process received signals.

U.S. Pat. No. 4,977,786, Capacitive Liquid Level Sensor, describes a commonly used level sensor. In this patent, probe and fluid are part of a circuit that generates a phase difference depending on the capacitance value of the probe and the fluid it contacts. The patent contemplates using an analog electronic means, which generates high frequency oscillations, for comparison purposes.

U.S. Pat. No. 5,049,826, Liquid Level Sensing Apparatus for use in Automatic Chemical Analysis, describes a level sensor that uses a balanced bridge with a probe as part of the bridge. When the probe touches the sample, the bridge is no longer balanced and a difference in the bridge is measured. The system described in the patent is run in the kHz region, and uses an analog electronic means for both comparison and generation of high frequency oscillations.

U.S. Pat. No. 5,083,470, Capacitive Liquid Level Sensor, describes a level sensor that is similar to that described in U.S. Pat. No. 4,977,786. In U.S. Pat. No. 5,083,470, an inductive coil is placed so that the probe protrudes through the coil so as to reduce the chance of false alarms.

U.S. Pat. No. 5,627,522, Automated Liquid Level Sensing System, describes a level sensor which is similar to that described in U.S. Pat. No. 5,275,951. U.S. Pat. No. 5,627,522 describes a bi-static system and not a reflection measurement.

SUMMARY OF THE INVENTION

By integrating impedance spectroscopy methods with fluid handling probes such as those employed by automated chemical and immunoassay analyzers, the invention enables rapid identification of a fluid and determination of its level within a test container. This is accomplished through measurement of the fluid's impedance spectrum and subsequent automated analysis of this spectrum to discern parameters of interest. As applied here, the method is comprised of four key functions to include: generation of an electronic signal, propagation of that signal along a pipette probe (which acts as a transmission line), detection of the signal reflected back from a point at or near the end of the probe toward the source through return loss measurement, and analysis of the reflected signal to discern parameters of interest.

A continuous or discrete electronic signal is generated and propagated along a pipette probe. As this probe is inserted into a fluid sample within a container and makes contact with the air-to-fluid interface, a change occurs in the characteristic impedance of the pipette probe with respect to the characteristic impedance of the pipette probe in free air. This impedance change, in turn, causes a change in the characteristics of the signal's energy that is reflected back. Through continuous measurement and analysis of this reflected signal, the air-to-fluid interface may be identified. Further, specific characteristics of the reflected signal may be used to identify the fluid as one among a limited set of possibilities. The method affords a number of advantages over conductance and capacitance methods. Specifically, the invention allows detection of fluid level using smaller volumes of fluid than is required for the conductance and capacitance methods. The fluid which is being measured and analyzed can be contained within "tube top" cups. In addition, spurious level detection upon fluid surface bubbles can be avoided. The behavior of the analyzer may be automatically adjusted to accommodate the fluid. And, only one conductor (the probe itself) is required.

It is therefore an exemplary embodiment of this invention to provide a system and method for identifying a fluid and determining its level in a container using impedance spectroscopy.

It is yet another exemplary embodiment of this invention to generate an electronic signal within or adjacent to a pipette probe, propagate the electronic signal towards a fluid sample in a container, and monitor the reflected signal, whereby the identity of that fluid as one among a limited set of possibilities is determined. This is accomplished by processing of the reflected signal to yield one or more derived parameters, followed by comparison of those same parameters with values previously established for known fluids of interest, wherein a match is determined by the closest correlation with comparable values previously established for a known fluid within the data set for a limited number of fluids.

It is yet another exemplary embodiment of the invention to provide a system that identifies a fluid as one among a limited set of possibilities by processing the reflected signal to yield one or more derived parameters, and which compares those same parameters with values previously established for known fluids of interest.

Another exemplary embodiment of the invention is to generate an electronic signal within or adjacent to a pipette probe, propagate the electronic signal towards a fluid sample in a container, and monitor the resultant reflected signal, whereby the air-to-liquid interface or "sample boundary" is determined from the portion of the signal which is reflected back (i.e., the propagated signal is known, the reflected signal is measured, and the ratio of the transmitted to reflected signal magnitudes is indicative of the air-to-liquid interface). A contact with the sample boundary would alter the impedance of the probe and thus the amplitude and phase of the reflected signal.

It is yet another exemplary embodiment of the invention to provide a system that determines the level of a liquid in a container by comparing characteristics of a reflected electronic signal to those of the original electronic signal propagated towards a liquid surface.

According to the invention, the identity of a fluid and its level in a container are determined using impedance spectroscopy. The invention is applicable, for example, to fluids in sample or reagent containers used by automated chemical and immunoassay analyzers. Further, it is applicable to most any application that employs a pipette probe for handling fluids in containers.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1:
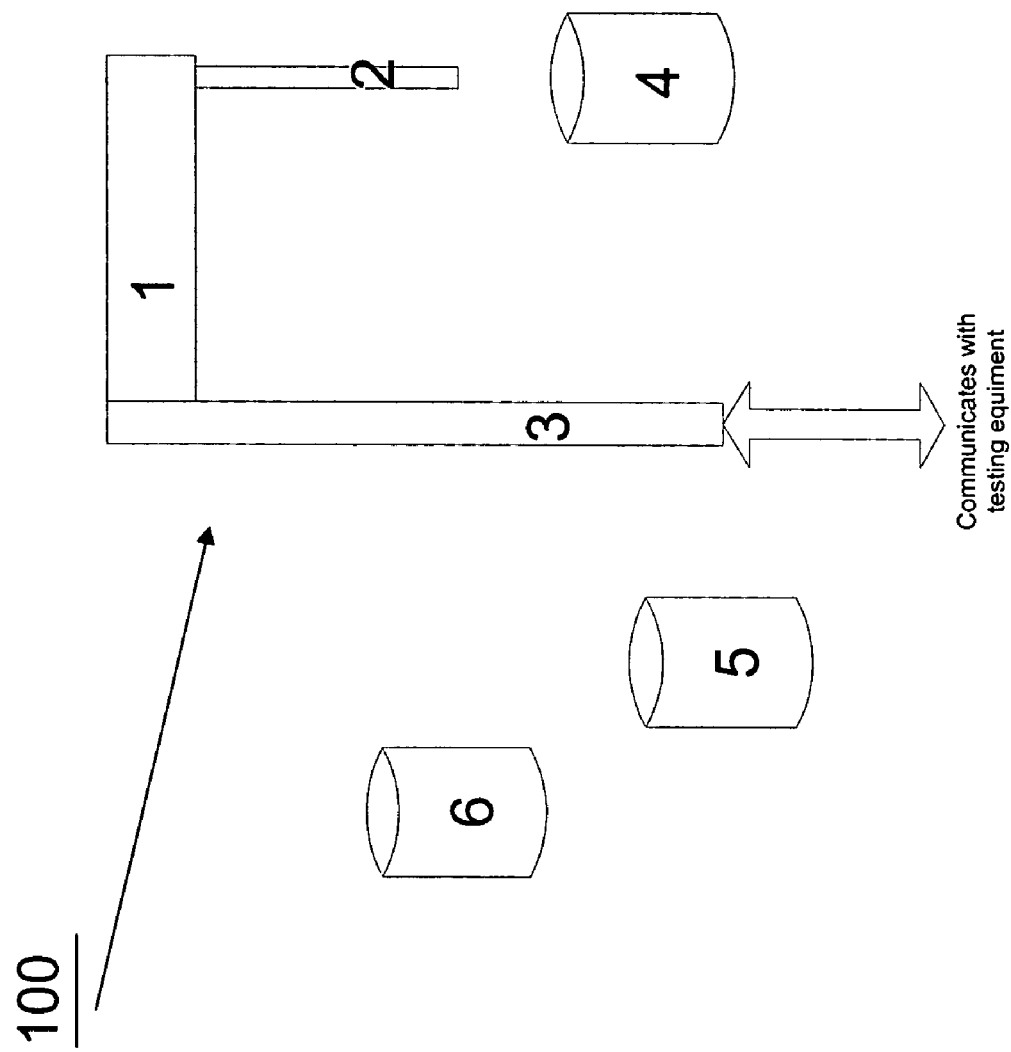
FIG. 1 is an illustration of the fluid level detector and analyzer assembly with pipette probe.

Referring now to the drawings, and more particularly to FIG. 1, there is shown a representation of a pipette subassembly 100 that may be used for example, in an automated chemical or immunoassay analyzer for storing and retrieving reagents, test samples, controls, or other fluids into or from a container such as a test tube. The reflectometer control subassembly I combines or contains some or all of the necessary electronic signal generation, detection and signal processing capability. The pipette probe 2 acts as a transmission line that propagates the electronic signal to the fluid sample in any one of several containers within, for example, an automated chemical analyzer or automated immunoassay analyzer. Specifically, the pipette probe 2 may measure fluid levels in any one of several containers to include, but not limited to, the dilution well 4, sample tubes 5 and/or reagent containers 6. In operation, the pipette probe 2 is movable both about axis 3 and is vertically moveable. This allows the pipette probe 2 to be lowered into the fluid to be measured as the reflected electronic signal is continuously monitored and analyzed. The fluid surface can thus be identified from relevant changes in the phase and/or magnitude of the reflected signal, or from parameters derived therefrom.

Figure 2:
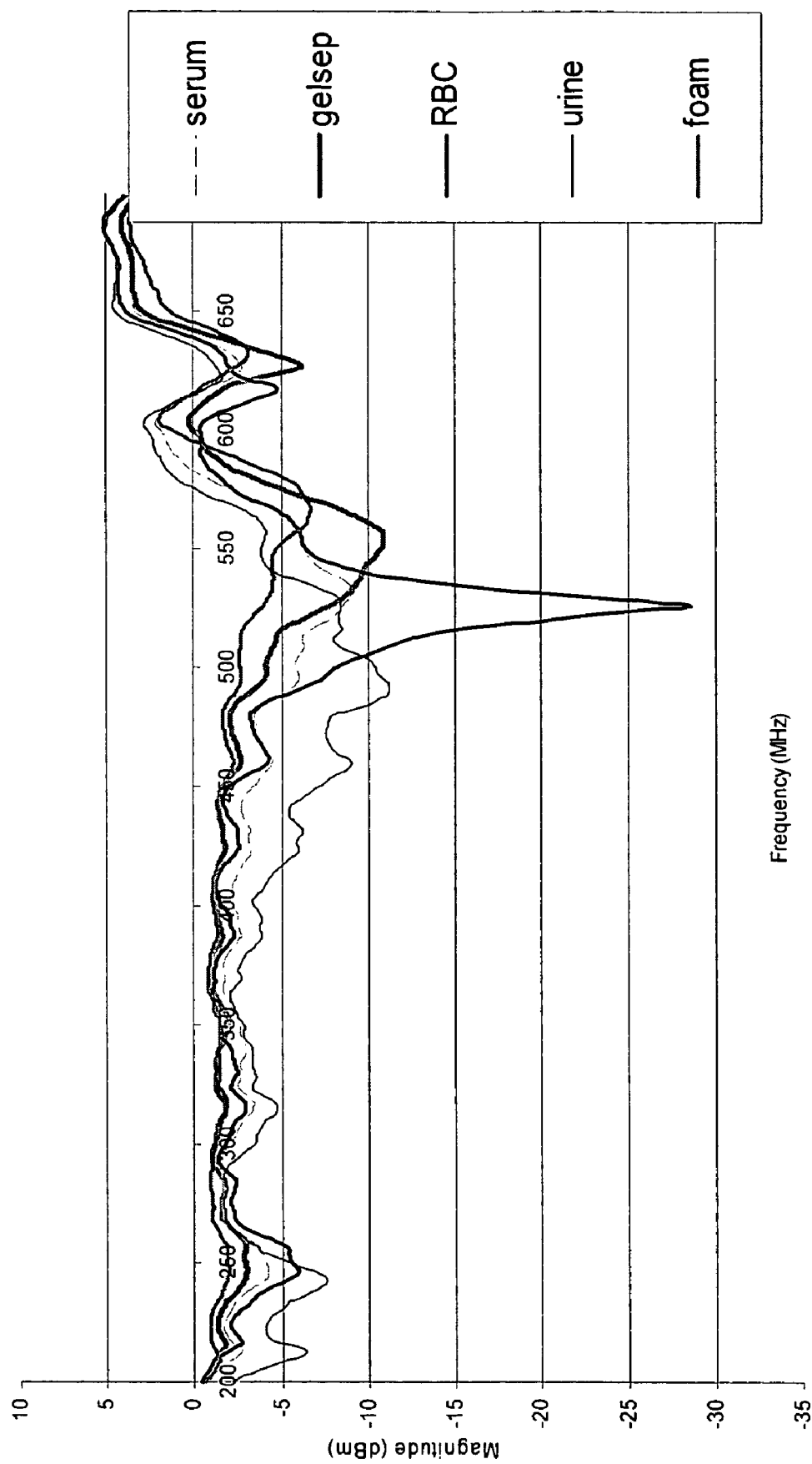
FIG. 2 is an illustration of possible impedance spectra of exemplary fluids.

An example of this change in magnitude of some of the possible limited set of fluids is shown in FIG. 2. The initial (or reference) reflected signal could be a white noise or swept signal which is normalized prior to plotting. As such, the initial (reference) reflected signal would appear as a straight line with magnitude of 0 dBm.

FIG. 2 provides an illustration of the magnitude plots of the limited set of possible fluids. It is the characteristics of these plots that the fluid level detector and analyzer can compare to determine which fluid is present in the container. These possible fluids include, but are not limited to, blood serum, blood plasma, gelsep, red blood cell layers, chemical reagents associated with immunoassay blood testing and foam atop fluid surfaces. FIG. 2 illustrates the different signal characteristics that may be presented by the various expected limited set of fluids. Identification of a fluid would involve determining which stored signal characteristics for different fluids best match the sensed signal characteristics (e.g., a plot of the measured signal characteristics could be compared to a set of stored plots for different fluids; the magnitude of a response at a specific frequency could be stored and the sensed value for a fluid of interest at the specific frequency could be compared against the responses of a defined limited set of fluids at that frequency, etc.).

The pipette probe 2 moves toward the fluid to be measured. The changes in the initial (reference) reflected signal are used to determine when the probe touches the fluid boundary. When the pipette probe 2 makes contact with the fluid, the invention further analyzes the reflected signal to calculate the magnitude of the reflected signal of the fluid. In the example of FIG. 2, the reflected signal magnitudes of some of the possible set of fluids have been plotted at each frequency to produce the waveforms shown. The characteristics (e.g., magnitudes at various frequencies) of the fluid under test can be compared to characteristics of the limited set of known possible fluids to determine which of these fluids the fluid under test is most likely to be. For example, a characteristic illustrated in FIG. 2 for gelsep at 526.25 MHz has a magnitude of −7.786 dBm and the exemplary plot for RBC at 526.25 MHz shows a magnitude of −28.667. Assuming the fluid under test had a magnitude of −22 dBm at 526.25 MHz, the fluid under test would most likely be RBC and not gelsep. Additionally, once the pipette probe 2 is in contact with or immersed in the fluid, the reflected electronic signal can be further analyzed against the original electronic signal and/or against the exemplary characteristics of the set of possible fluids to discern additional information such as but not limited to phase.

A classic reflectometer comparative measurement technique is preferably employed, by observing changes in the received (reflected) signal relative to the reference (incident) signal. The reference signal is measured as the magnitude and phase of the reflected signal when the pipette probe 2 is not immersed in any liquid, which is typically at the top of the linear travel of pipette probe 2. The quantity calculated is a measurement of the circuit's return loss while in air. Because of the distance traveled by the signal, some change may occur in the signal originally propagated, and in the reflected signal when the probe is not in contact with the fluid to be measured. It is the reflected signal when the pipette probe 2 is not immersed or in contact with the fluid that is measured and the magnitude and phase calculated to be used as the reference signal for comparison to the reflected signal after the pipette probe 2 has made contact with the fluid to be measured. Thus, the reference reflected signal may vary from the signal that was generated and propagated toward the fluid to be measured.

The formation of bubbles and/or foam is a typical event that occurs on the surface of liquids presented to automated chemical analyzers and/or automated immunoassay analyzers. Employing conventional conductance or capacitance methodologies, these bubbles can trigger a spurious fluid level detection event on the foam surface (as opposed to the fluid surface) due to weak connection with the ground plane. In turn, this can cause the pipette probe to begin its aspiration cycle while immersed in the bubbles/foam, ultimately leading to failure of volumetric fluid aspiration.

In contrast, the invention is not sensitive to weak ground plane connection because the impedance of the bubbles/foam contributes only weakly to the reflected signal. Thus, as the probe contacts the fluid, the impedance of the circuit is significantly changed and the return loss is altered accordingly. The invention can easily distinguish these changes as exhibited in the FIG. 2.

The invention affords an additional advantage in its ability to discern, digitize and analyze spectral information from the reflected signal. This enables the application of software algorithms to identify relevant changes in the signal (or parameters derived therefrom) that occur when the probe is inserted into fluid, foam or other materials. More particularly, substantial differences in reflected signals have been demonstrated at the air-foam, foam-liquid and air-liquid boundaries. A signal-processing algorithm can thus be designed to select or differentiate only the liquid boundary that must be accurately identified to enable proper fluid aspiration. The ability to selectively ignore the foam boundary is an advantage in that it can avert failures of volumetric fluid aspiration that would otherwise occur.

Figure 3:
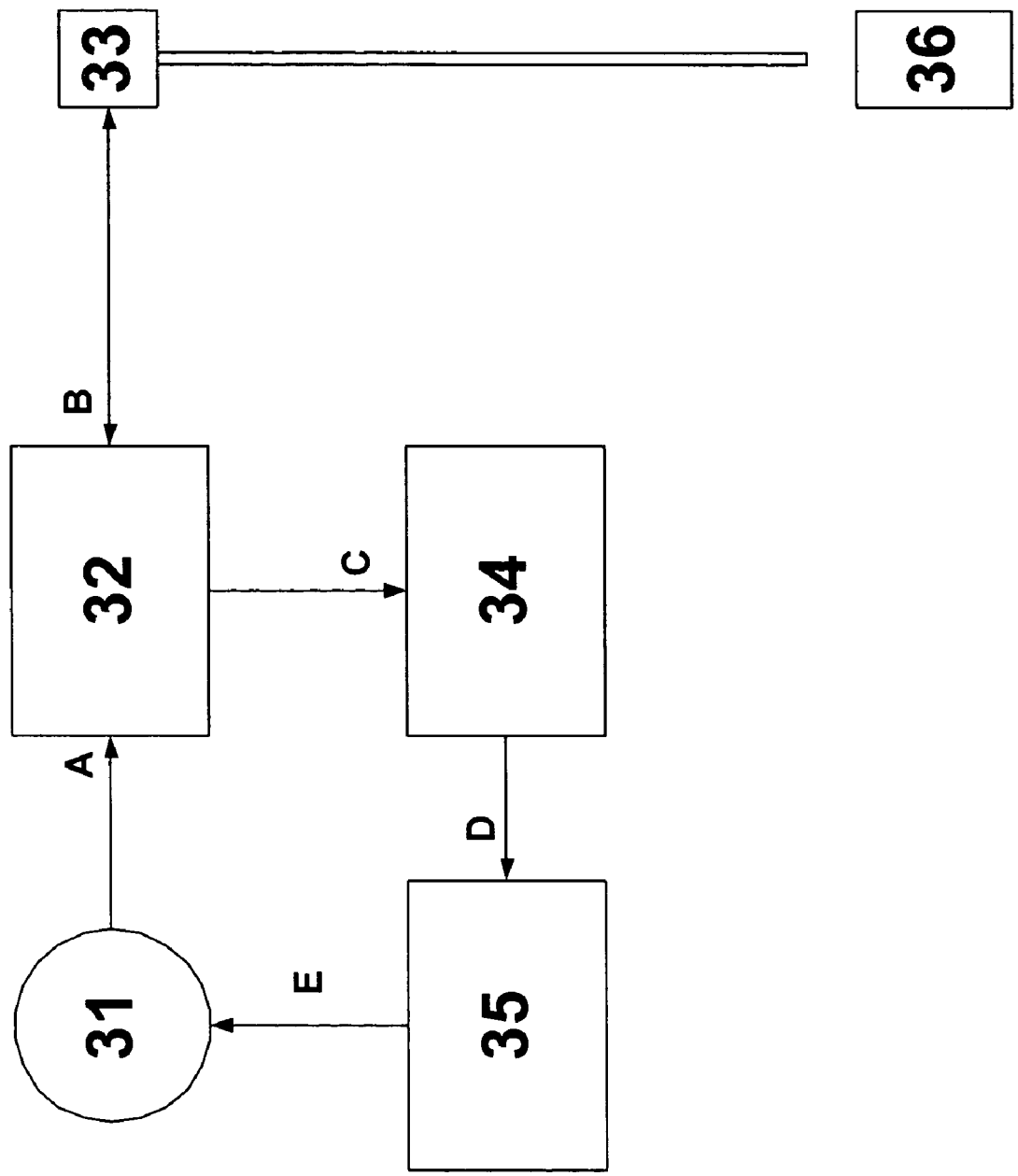
FIG. 3 Simplified block diagram of fluid level detector and analyzer system

FIG. 3 provides a block diagram of the invention. Subassembly 31 represents the signal excitation source, whose output signal characteristics are controlled by a microprocessor/microcontroller subassembly 35, via port E. Since a variety of signal source types can be implemented for impedance spectroscopy, such as but not limited to band-limited white noise, shaped pulse, swept frequency, or other signal type, subassembly 31 may include any combination of these signal excitation source types.

Still referring to FIG. 3, subassembly 32 is a return loss bridge, or directional coupler. This device passes the excitation, or incident, signal from subassembly 31 via port A, to pipette probe subassembly 33 via port B. The incident signal travels down the path of the probe in subassembly 33, and a portion of the incident wave is reflected back along the path of the probe in subassembly 33, into subassembly 22 port B. Subassembly 32 then isolates the reflected signal energy via port C. This reflected signal is then presented to the detector circuitry of subassembly 34. Subassembly 34 may include but is not limited to Analog to Digital converters that digitize the signal into a data stream.

Subassembly 34 presents the data via Port D to the subassembly 35. Subassembly 35 may be a microprocessor or microcomputer or similar device. Subassembly 35 contains all the suitable algorithms that are needed to process and analyze the data stream for the identity of a fluid and its level in a container (subassembly 36), as well as suitable algorithms needed for the control of the signal excitation source of subassembly 31.

Figure 4:
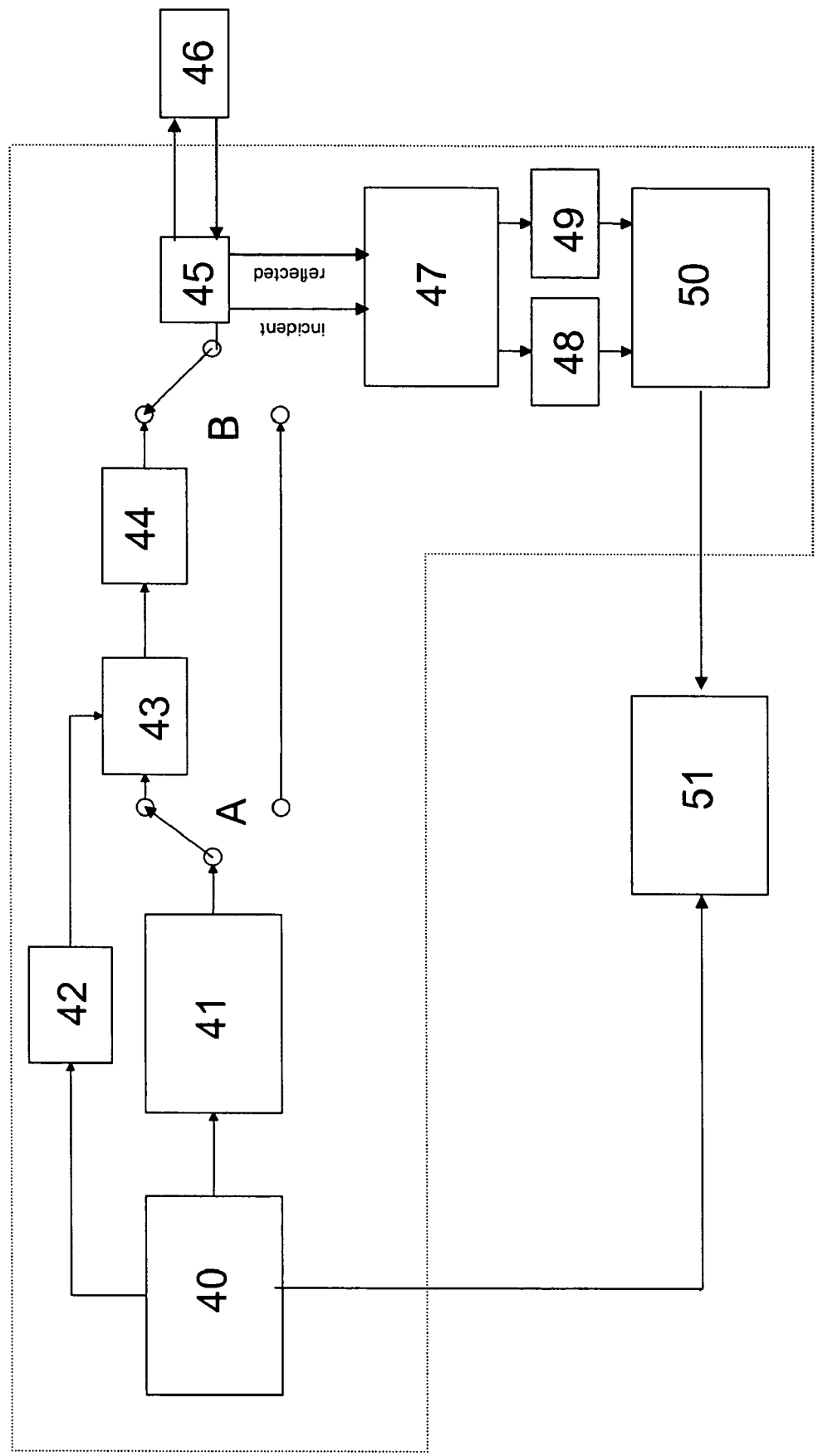
FIG. 4 a block diagram of an embodiment of the fluid level detector and analyzer.

FIG. 4 provides a detailed block diagram of an exemplary reflectometer control subassembly 1 (it being understood that different circuitry and components could be used to accomplish the transmission line reflectometry methodology for identifying a fluid and/or detecting the fluid level in a container within the practice of this invention) The elements shown within the dotted line of FIG. 4 are those elements that could be located on the reflectometer control subassembly 1 of the pipette subassembly 100 shown in FIG. 1. Element 46 is the sample and/or fluid under test and is not part of the reflectometer control subassembly 1. The signal lines shown on FIG. 4 between element 45 and element 46 would be propagated down the pipette probe 2. Finally, element 51 could be located either within the pipette arm 3 or the reflectometer control subassembly 1.

Still referring to FIG. 4, the control electronics 30 accepts test request data from the system interface 51 and configures the reflectometer subassembly 1 to provide the appropriate electronic signal. This signal propagates through a directional coupler 45 and passes the propagated signal to the load 46 (the fluid under test). A returned signal passes back through another port in the directional coupler 45 and is provided to the ratiometric gain detector 47 as the reflected signal. The incident signal is also provided to the detection circuit in order to perform the relative measurement. A/D converters 48 and 49 then digitize the processed signal, and the resulting digital data are forwarded to digital signal processor 50. There, software algorithms process the received signal to discern characteristics of interest (e.g., measured plots and/or values at various frequencies, etc.) and these are transmitted to the system interface 51 for use by the chemistry or immunoassay analyzer. It should be noted that simpler embodiments such as analog filters and comparators might be substituted for A/D converters 48 and 49 and digital signal processor 50 for some applications.

Signal Generation

The direct digital synthesizer 41 generates a "white noise" signal, for example, in the range of 200-400 MHz. The local oscillator 42 preferably produces a 1 GHz signal. The specific frequency range is preferably selected depending upon the type of fluid to be measured. For example, one fluid might best be monitored in the range of 200-400 MHz, while the 400-700 MHz range might be suitable for a different fluid. Thus, the control electronics 40 manages the switches A and B to allow the direct digital synthesizer 41 signal to be mixed at mixer 43 with the signal from the local oscillator 42. The signal from the mixer 43 is smoothed by filter 44 to eliminate sidebands produced by mixer 43. This output signal is provided to the directional coupler 45. The signal output from filter 44 is preferably in the 400-700 MHz signal range depending on the signal generated by the direct digital synthesizer 41 as selected by the control electronics 40. In the event that the lower frequency range is desired, the control electronics 40 configures the reflectometer elements to bypass the mixer 43 and filter 44 so as to provide, for example, the 200-400 MHz frequency signal to the directional coupler 45. The output signal provided to the directional coupler 45 from either the filter 44, or from the direct digital synthesizer 41, is used by the ratiometric gain detector 47 as the incident RF signal.

Signal Propagation and Detection

The pipette probe acts as a transmission line that propagates the output (incident) signal down the pipette probe to sample 46. For simplicity, this embodiment describes level measurement of the sample container. However, the pipette probe 2 is appropriate to interrogate fluid levels within any container of, for example, an automated chemical or immunoassay analyzer. Types of containers may include, but are not limited to, sample containers, dilution wells, reagent containers, etc. The reflected electronic signal from the sample fluid is received by the directional coupler 45, and forwarded to the ratiometric gain detector 47. The directional coupler 45 ensures that the reflected signal does not corrupt the incident signal.

The Gain detector 47 forms a ratio to enable measurement of the magnitude and phase of the reflected signal relative to the incident signal. The voltage of the sinusoidal signal is a complex entity identified by the equation $(e^{i\omega t}-e^{-i\omega t})/2i$, where $\omega$ is the radial frequency of the signal and is equal to $2*\Pi*f$ (frequency). As such, the return loss is measured using the reflectometer comparative measurement technique and the complex reflection coefficient is computed. The complex reflection coefficient is defined as $$\Gamma = \rho \angle \Phi = \frac{(Z_1 - Z_0)}{(Z_1 + Z_0)}$$

where $\rho$ is the return loss which is the magnitude of 51 $|\Gamma|$, z is the return loss that is the magnitude of the impedance of the load and is detected by analog/digital converter 48, $Z_1$ is the impedance of the load and $Z_0$ is the impedance of the source (typically 50Ω). $Z_1$ is an impedance which is a combination of a resistance and a reactance. This impedance is defined as $Z_1=R_1+I(X_c+X_1)$ where $X_c$ is the capacitive component of the load, $X_1$ is the inductive portion and $R_1$ is the resistive portion. The phase angle $\Phi$ of the complex reflection coefficient is defined arc tan $((X_c+X_1)/R)$, and is detected by analog/digital converter 49. The values for each parameter (magnitude and phase) are measured for each swept frequency, digitized and provided to digital signal processor 50 for analysis. Finally, the output of digital signal processor 50 is made available through system interface 51 for use by an instrument such as a chemistry or immunoassay analyzer.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An impedance spectroscopy method for performing one or more of identifying a fluid and determining a level of said fluid in a container, comprising the steps of:
   positioning a pipette probe above said level of said fluid in said container;
   generating an incident electronic signal in a specific frequency range from a source;
   propagating said incident electronic signal along a length of said pipette probe;
   detecting a reflected electronic signal reflected back toward the source;
   comparing characteristics of said reflected electronic signal with those of said incident electronic signal; and
   either or both i) identifying said fluid in said container using information derived from said comparison and ii) determining said level of said fluid in said container using information derived from said comparison.

2. The method of claim 1 wherein said positioning step includes translating said pipette probe along a longitudinal axis towards said level of said fluid.

3. The method of claim 1 wherein said incident electronic signal from said generating step is a sinusoidal swept frequency signal in the 0.42 to 1.5 meter ISM band identified by the equation $(e^{i\omega t}-e^{-i\omega t})/2i$ where $\omega=2\pi f$, f is frequency and I is (−1).

4. The method of claim 1 wherein said detecting step is accomplished through transmission line reflectometry.

5. The method of claim 1 wherein said comparing step includes determination of an impedance spectrum of said liquid.

6. The method of claim 1 wherein said determining step entails derivation of parameters used to determine said level of the contained fluid.

7. The method of claim 1 wherein said comparing step i) identifies said fluid in said container.

8. The method of claim 1 wherein said comparing step ii) determines said level of said fluid in said container.

9. The method of claim 1 wherein said comparing step both i) identifies said fluid in said container, and ii) determines said level of said fluid in said container.

10. The method of claim 1 wherein said electronic signal is of a single frequency.

11. The method of claim 1 wherein said electronic signal is of a narrow range of frequencies.

12. A method for identifying a fluid and determining a level of said fluid in a container by applying impedance spectroscopy methods, wherein applying impedance spectroscopy methods includes inserting a fluid handling probe into the fluid in the container, wherein applying impedance spectroscopy methods further includes comparing an incident signal applied to the fluid handling probe with a reflected signal.

13. The method of claim 12 wherein applying impedance spectroscopy methods further includes continuously monitoring for a difference between the incident signal and the reflected signal as the fluid handling probe is inserted.

14. A system for either or both identifying a fluid and determining a level of said fluid in a container comprising:
   a translating drive which moves a pipette probe along a longitudinal axis;
   an electronic device which generates and propagates an incident electronic signal along a length of said pipette probe;
   a detector which detects an electronic reflected signal from said fluid in said container;
   a return loss bridge which separates said incident electronic signal from said reflected electronic signal and routes said incident electronic signal and said reflected electronic signal to a detector; and
   a computer resource that either or both i) identifies said fluid, ii) determines a level of said fluid in said container, through comparison of said incident electronic signal and said reflected electronic signal.

15. A system for determining a level of said fluid in a container comprising:
   a translating drive which moves a pipette probe along a longitudinal axis;
   an electronic device which generates and propagates an incident electronic signal along a length of said pipette probe;
   a detector which detects an electronic reflected signal from said fluid in said container;
   a return loss bridge which separates said incident electronic signal from said reflected electronic signal and routes said incident electronic signal and said reflected electronic signal to a detector; and
   a comparator that determines a level of said fluid in said container through comparison of said incident electronic signal and said reflected electronic signal.

16. A method for identifying a fluid and determining a level of said fluid in a container by applying impedance spectroscopy methods, wherein applying impedance spectroscopy methods includes inserting a fluid handling probe into the fluid in the container, wherein applying impedance spectroscopy methods further includes detecting an air/fluid interface based on detecting a change in a reflected signal applied to the fluid handling probe as the fluid handling probe is inserted into the fluid.

17. An impedance spectroscopy method for performing one or more of identifying a fluid and determining a level of said fluid in a container, comprising the steps of:

positioning a pipette probe above said level of said fluid in said container;

generating an incident electronic signal in a specific frequency range from a source;

propagating said incident electronic signal along a length of said pipette probe;

detecting a reflected electronic signal reflected back toward the source;

comparing characteristics of said reflected electronic signal with those of said incident electronic signal to determine of an impedance spectrum of said liquid and deriving parameters from said impedance spectrum; and either or both i) identifying said fluid in said container using the parameters derived from said comparison and ii) determining said level of said fluid in said container using information derived from said comparison.

* * * * *

UNITED STATES PATENT AND TRADEMARK OFFICE
CERTIFICATE OF CORRECTION

| | | |
|---|---|---|
| PATENT NO. | : 7,621,181 B2 | Page 1 of 1 |
| APPLICATION NO. | : 11/402254 | |
| DATED | : November 24, 2009 | |
| INVENTOR(S) | : Cammarata et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Twenty-sixth Day of October, 2010

David J. Kappos
*Director of the United States Patent and Trademark Office*